United States Patent
Häupl et al.

(10) Patent No.: US 7,441,952 B2
(45) Date of Patent: Oct. 28, 2008

(54) METHOD AND SYSTEM FOR X-RAY DIAGNOSIS OF AN EXAMINATION OBJECT

(75) Inventors: Rainer Häupl, Krummennaab (DE); Claus-Günter Schliermann, Kemnath (DE)

(73) Assignee: Siemens Aktiengesellschaft (DE)

( * ) Notice: Subject to any disclaimer, the term of this patent is extended or adjusted under 35 U.S.C. 154(b) by 0 days.

(21) Appl. No.: 11/600,647

(22) Filed: Nov. 16, 2006

(65) Prior Publication Data

US 2007/0121791 A1    May 31, 2007

(30) Foreign Application Priority Data

Nov. 22, 2005    (DE) .................. 10 2005 055 653

(51) Int. Cl.
*H01J 31/50*    (2006.01)
*H05G 1/02*    (2006.01)

(52) U.S. Cl. ....................... 378/189; 378/193

(58) Field of Classification Search .............. 378/167, 378/170, 189, 196–197, 205–207, 193, 195, 378/198

See application file for complete search history.

(56) References Cited

U.S. PATENT DOCUMENTS 4,417,356 A * 11/1983 Hoffman ................ 378/181

6,851,851 B2 * 2/2005 Smith et al. ............. 378/189
2006/0083353 A1 * 4/2006 Boomgaarden ......... 378/196
2006/0126795 A1 * 6/2006 Lumma ................... 378/193

FOREIGN PATENT DOCUMENTS

| DE | 103 47 740 A1 | 6/2005 |
| DE | 103 47 738 A1 | 9/2005 |
| JP | 2004073354 A * | 3/2004 |

OTHER PUBLICATIONS

German Office Action for DE 10 2005 055 653.1-35 dated Aug. 31, 2006 and English translation.

* cited by examiner

*Primary Examiner*—Irakli Kiknadze
(74) *Attorney, Agent, or Firm*—Brinks Hofer Gilson & Lione

(57) ABSTRACT

A system and method for X-ray diagnosis of an examination object is provided. The system includes a component that is movable relative to a stretcher for the examination object and at least one predeterminable set stop position for the component. A position ascertaining device is operative to ascertain a position of the component. A braking device is operative to brake the movable component. A control unit is connected to the position-ascertaining device and to the braking device. The braking device is activatable as a function of the position of the component relative to the stop position.

18 Claims, 2 Drawing Sheets

METHOD AND SYSTEM FOR X-RAY DIAGNOSIS OF AN EXAMINATION OBJECT

This application claims the benefit of DE 10 2005 055 653.1 filed Nov. 22, 2005, which is hereby incorporated by reference.

BACKGROUND

1. Field

The present embodiments relate to a system for X-ray diagnosis of an examination object and a method for performing an X-ray diagnosis on an examination object.

2. Related Art

The present embodiments relate generally to improving the positioning of components in an X-ray system. X-ray systems remain a significant instrument for medical diagnosis and patient monitoring, regardless of the development in the field of medical technology and in particular imaging processes, such as computed tomography and magnetic resonance tomography. X-ray examinations are used in diagnosing bone fractures, tumors, cysts, calcifications, and air inclusions. X-ray examinations are also used in angiographic examinations for viewing the vascular system of a patient. During interventional surgeries, introduced medical instruments can also be located using X-ray examinations. By reducing the radiation dose used for the X-ray examinations of the patient, particularly by technological progress, still other fields where X-ray diagnosis can be employed are gained.

Flexible positioning of components of an X-ray system, for example, X-ray sources and X-ray detectors, may be significant in the field of medical diagnosis. A greater field of use for an X-ray device may be obtained by using components with increased flexibility.

In the case of X-ray examinations that are performed frequently, the same positions or stop positions of the components, for example, the X-ray detector and the X-ray source, are provided. One possible stop position for the X-ray examinations can be the location of an X-ray source above a patient's stretcher, so that the X-radiation vertically strikes, for example, the thorax of a patient positioned on the stretcher. The X-radiation is detected underneath the patient by an X-ray detector. In another possible position, the x-ray source and X-ray detector are rotated by 90°. Certain angular combinations of the X-radiation and the surface of the X-ray detector are also advantageous.

From the user manual for use of the ceiling-mounted support arm 3D-T.O.P., a tripod for an X-ray system is known which predetermines a stop position of an above-table X-ray emitter by detent positions in a longitudinal and a transverse travel path. In the user manual, the stop position is called the imaging position. The motion of the above-table X-ray emitter is manually operated by medical personnel. The detent positions are predetermined by touch detents or electromechanical detent traps. This has the disadvantage that for adjusting a fixed stop position, mechanical adjustment of the touch detents or electromechanical detents is necessary.

SUMMARY

In one embodiment, a system for X-ray diagnosis of an examination object includes a position-ascertaining device that ascertains a position of the component, a braking device that brakes the movable component, and a control unit, which is connected to the position-ascertaining device and to the braking device. The braking device is operative as a function of the position of the component relative to the stop position.

For example, a rapid motion of the component, into a defined stop position, is possible. The component may include, but is not limited to, the X-ray emitter, the X-ray detector, or a plurality of suitable devices. The motion of the component to the stop position, which includes displacements and/or rotations of the component, is automatically detected by the controller via the position-measuring device.

In one embodiment, the position-measuring device is a sensor system. At least one sensor is mounted on each component to be moved of an X-ray system. The position of the sensor can be detected and optionally ascertained by a wireless connection to a sensor interrogation system. Alternatively, absolute value transducers or rotary angle transducers can be used for detecting the position of a component. The use of linear measuring systems, for example, magnetorestrictive sensors or magnetoresistive sensors, is equally possible. The ascertained position of the component is recorded in a coordinate system, which includes the stop positions for the various components that are also detected. In one embodiment, the stop positions are set using a user interface, for example, a display or control switch, on the X-ray device or on a personal computer that is connected to the controller. A three-dimensional stop region around the stop position is predetermined. In one embodiment, the three-dimensional stop region is set via the user interface. For example, the stop positions as well as the predetermined stop region around the stop position can be preset by the equipment manufacturer or adapted to the wishes of the user at the time the system is first put into use, or at any suitable time.

In one embodiment, the braking device is activated when the component arrives at a predetermined stop region around the stop position. The braking device, after its activation, brakes the motion of the component until the component comes to a stop. The activation of the braking device can be done by the user and/or by the control unit. For example, in one embodiment, a user can move the X-ray emitter into a stop region and activate the brake by releasing a control key. In this embodiment, the X-ray emitter can be moved into the stop position via the control unit and the position-ascertaining device, using a drive mechanism.

In an alternative embodiment, the components speed is detected. For example, the speed and position of the component can be ascertained. The speed can optionally be used in addition as a criterion for activating the braking device. In one embodiment, by exceeding a predetermined limit speed, for example, in a surrounding region outside the predetermined stop region of the stop position, a stop position can be overtaken without activating the braking device. Conversely, the braking device is activated, when the predetermined limit speed in a surrounding region outside the predetermined stop region of the stop position is not exceeded, and the component reaches the predetermined stop region of the stop position. Storing the value for a limit speed in memory can be done in the controller. In one embodiment, the speed is detected using sensors that detect the quantitative change in position of a moving component.

In one embodiment, additional and/or changed stop positions can be used, without making a structural change in the system.

In one embodiment, a driving device for that drives the component is operatively connected to the control unit in such a way that the component is movable to the stop position. The stop position is set without a manual drive, for example, a drive generated by the user, of the motion of the component. In an alternative embodiment, a combination of different drives may also be used, such as a manual and a motor drive device. For instance, by manual driving, the component can experience an abrupt (coarse) transition into or adjacent to the stop position, however, the motor drive has a smooth (fine) transition into the stop position. In one embodiment, the driving device moves the component with an only slight increment width, and the position ascertainment is done by the controller in real time. In this embodiment, the stop position is reached with high accuracy.

In one embodiment, a coupling device is disposed between the driving device and the movable component. In this embodiment, the propulsion to be transmitted to the component can be metered and adapted to the position of the components, which increases the accuracy of the positioning.

In one embodiment, at least two different stop positions are set. In this embodiment, the X-ray emitter is rotationally movably supported, and a first and second stop position can be set in which the X-radiation can be projected in the vertical and horizontal directions, respectively. The vertical direction is oriented parallel to the direction of gravity, and the horizontal direction is perpendicular to the direction of gravity. Horizontal and vertical stop positions of the X-ray emitter are often used for X-ray examinations and should therefore be easy to adjust. The present embodiments are not limited to horizontal and vertical stop positions, for example, other stop positions can be set without effort by user control of the controller. For example, these can include the setting of certain angles of the X-radiation relative to the detection face of the X-ray detector. Conventionally, such angles could be manually set by the user only with a great deal of difficulty.

In one embodiment, the drive unit is embodied as an electric motor and/or the braking device is embodied as a permanent-magnet brake. An electric motor is easy to dimension in terms of its size and power and can easily be positioned on the system. The electric motor is simple to control. In an X-ray system, a plurality of electric motors may be present for driving rotations and displacements of various components, such as displacing support arm carriages or rotating components that are secured to the support arm.

In one embodiment, the braking device is an electromagnetic braking device. In this embodiment, there is less wear on the braking device but with good controllability. The electromagnetic braking device maybe embodied as, for example, a permanent-magnet brake. In this embodiment, fixation of the component in a stop position after it stops can be achieved in addition to braking the motion of the component. No additional fixation device for the component after it stops is therefore required. In this embodiment, an energy supply for the X-ray diagnosis system is not a prerequisite for the function of the permanent-magnet brake, which enhances the safety of the X-ray diagnosis system. In an alternative embodiment, a friction brake, which is released magnetically and actuated with spring force, can be used. In this alternative embodiment, the braking device has, for example, the advantages of the permanent-magnet brake, but it does have greater wear from stress by mechanical brake components such as a spring. In another embodiment, a magnetic brake is used, in which a magnetic field and hence the braking action can be controlled, for example, via a coil current. In this embodiment, the braking action is simple to control. The prerequisite for a magnetic brake is a power supply to the brake.

In an alternative embodiment, a fixation device and a braking device can be provided separate from one another. In this embodiment, the fixation device is embodied solely for fixation or, for example, holding a component in a certain position. For example, in one embodiment, an eddy current brake, which operates without wear, may be present along with a fixation device that is embodied as a permanent-magnet brake, so as to brake motions of the component.

In one embodiment, the component is moved manually and/or by motor in the direction of the stop position, and the position of the component is detected; and that the moving component is braked as soon as the position of the component reaches a predetermined stop region around the stop position. Accordingly, wear-free, rapid positioning of movable components can be made possible. Existing stop positions can be changed without effort and new stop positions can be defined, by supplying the altered or new stop positions to the controller.

DETAILED DESCRIPTION

Figure 1:
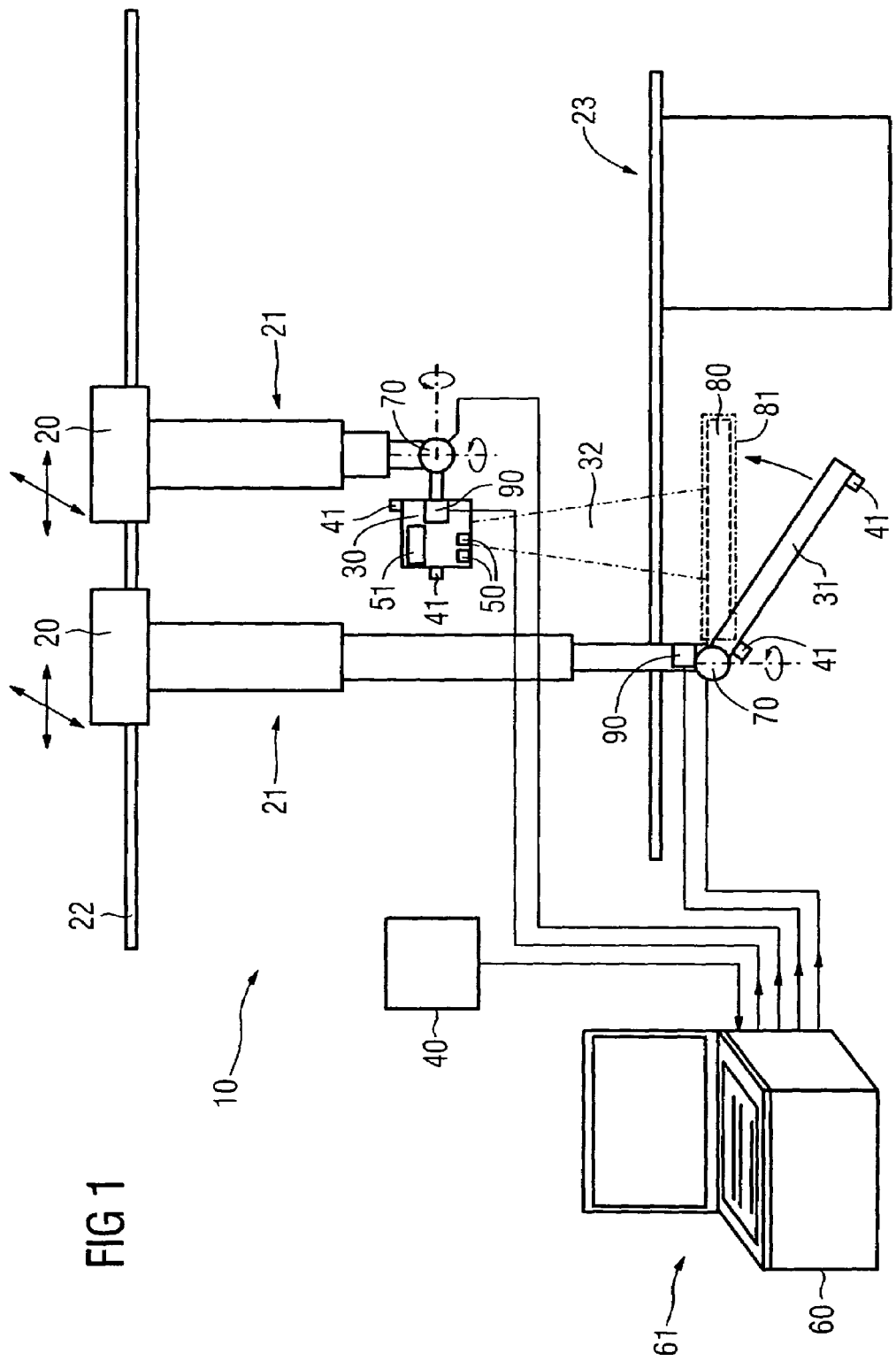
FIG. 1 is a schematic side view of one embodiment of a system for X-ray examination.

In one embodiment, as shown in FIG. 1, an X-ray diagnosis system 10 includes a ceiling-mounted guide rail system 22. Two carriages 20 are movably supported on this ceiling-mounted guide rail system 22 in such a way that they can be displaced arbitrarily and independently of one another in a plane parallel to the ceiling. A stretcher or patient support 23 that supports an examination object is positioned below the ceiling-mounted guide rail system 22. Telescoping arms 21 are secured to the respective carriage 20. The telescoping arms 21 are extended to adapt (e.g., alter the length) to the requirements (i.e. height) of the medical examination. In one embodiment, the end of one of the two telescoping arms 21 includes an X-ray emitter 30 supported rotatably about two axes of rotation, and the end of the other of the two telescoping arms 21 includes an X-ray detector 31 supported rotatably about two axes of rotation.

In one embodiment, stop positions for the X-ray emitter 30 and the X-ray detector 31 are preset. For the X-ray diagnosis system 10 shown in FIG. 1, two stop positions each for the X-ray emitter 30 and for the X-ray emitter 31 are defined. For example, a vertical stop position of the X-ray emitter 30 and an associated horizontal stop position 80 of the X-ray detector 31. In addition, a horizontal stop position of the X-ray emitter 30 and an associated vertical stop position of the X-ray detector 31 are possible; however, these are not shown in FIG. 1. Once the X-ray emitter 30 and the X-ray detector 31 have assumed their associated stop positions, an X-ray examination can be started. During the X-ray examination, an X-ray region 32 develops between the X-ray emitter 30 and the X-ray detector 31. The X-ray detector 31 detects the region to be examined of the examination object positioned on the stretcher 23. Depending on the field in which the X-ray diagnosis system 10 is used, other suitable stop positions can be obtained. For example, the present embodiments are not limited to the horizontal stop position and vertical stop position shown in FIG. 1 or described above.

In one embodiment, the stop positions may be changed, or supplemented with new stop positions, via an input/output device 61 that is operatively connected to the control unit 60. Changing and/or resetting stop positions is done by user input of control parameters for the various components 30 and 31.

In FIG. 1, the X-ray emitter 30 is in the vertical stop position. However, the X-ray detector 31 is not yet in the associated horizontal stop position 80. In this embodiment, the X-ray detector 31 is first moved into the stop position 80 before an examination is performed. In one embodiment, position sensors 41 are disposed on the X-ray emitter 30 and the X-ray detector 31. The position sensors 41 belong to a position-ascertaining device. The position-ascertaining device includes a position data transceiver 40. The position data transceiver 40 communicates in wireless fashion with the position sensors 41 on the X-ray emitter 30 and on the X-ray detector 31. The position-ascertaining device detects the location and position of the X-ray emitter 30 and of the X-ray detector 31 and possibly any change in the position using the position sensors 41 and the position data transceiver 40. In one embodiment, the detected position data is delivered to a control unit 60. The position of the X-ray emitter 30 and of the X-ray source 31 can be ascertained from the position data supplied to the control unit 60 using a coordinate system stored in memory in the control unit 60. Optionally, this can already be performed in the position-ascertaining device.

In one embodiment, the X-ray detector 31 is fixed in the associated horizontal stop position 80. In this embodiment, a fixation device fixes the X-ray detector 31 and/or of the X-ray emitter 30 in an arbitrary position. In FIG. 1, the fixation device is illustrated as a braking device 70. Alternatively, a fixation device and a braking device 70 may be embodied as separate components, possibly spatially separate devices. To move the X-ray detector 31 into the stop position 80 shown in FIG. 1, a user of the X-ray diagnosis system 10, such as the medical technicians present or a physician, releases the braking device 70 by operating a control switch 50. The user then rotates the X-ray detector 31 in the direction of the desired horizontal stop position 80 of the X-ray detector 31. The motion of the X-ray system 31, which is driven by the user, is detected by the position-ascertaining device and delivered to the control unit 60. In one embodiment, a stop region 81, which surrounds the stop position 80, is stored in a memory in the control unit 60. If the X-ray detector 31 arrives in the stop region 81 of the stop position 80, the control unit 60 activates a braking device 70, which is, for example, a permanent-magnet brake. The permanent-magnet brake 70 brakes the rotation of the X-ray detector 31. The X-ray detector 31 therefore comes to a stop at the predetermined stop position 80.

In one embodiment, a wide stop region 81 is selected. For example, a stop region 81 is selected that is wider than the stop region 81 indicated in FIG. 1. In this embodiment, the accuracy of the braking operation is increased. During the braking, the braking force of the permanent-magnet brake 70, taking into account the ascertained position of the X-ray detector 31 within the stop region 81, can be controlled in such a way that the X-ray detector 31 comes to a stop precisely at the stop position 80.

In one embodiment, the motion of a component 30 or 31 into a previously set stop position, for example, the stop position 80 of the X-ray detector 31, as well as the selection of different stop positions can be set via a user interface. For example, if a thorax examination is to be completed, then the stop positions for a thorax examination are set using the user interface. The characteristics of a thorax X-ray examination differ from those of a foot fracture X-ray examination. For example, the characteristics to be set are the position of the support carriage 20, the length of the telescoping arms 21, and the stop position of the X-ray emitter 30 and X-ray source 31. Such examination scenarios may be stored in memory in a data processing system, not shown, and supplied to the control unit 60 after selection of an examination scenario by a user. The user interface can include an actuation key on, for example, a touch screen or a display 51, which is associated with the control switch 50. New stop positions can thus be defined quickly and simply. Optionally, the entire motion of the X-ray detector 31 or X-ray emitter 30 can be driven by a drive mechanism 90, which is embodied here as an electric motor. The control unit 60 can control the electric motor 90 in such a way that the X-ray detector 31 or X-ray emitter 30 approach the defined respective stop positions. The stop positions may also include the position of one or more support arm carriages 20, the length of the telescoping arm 21, and the like.

Figure 2:
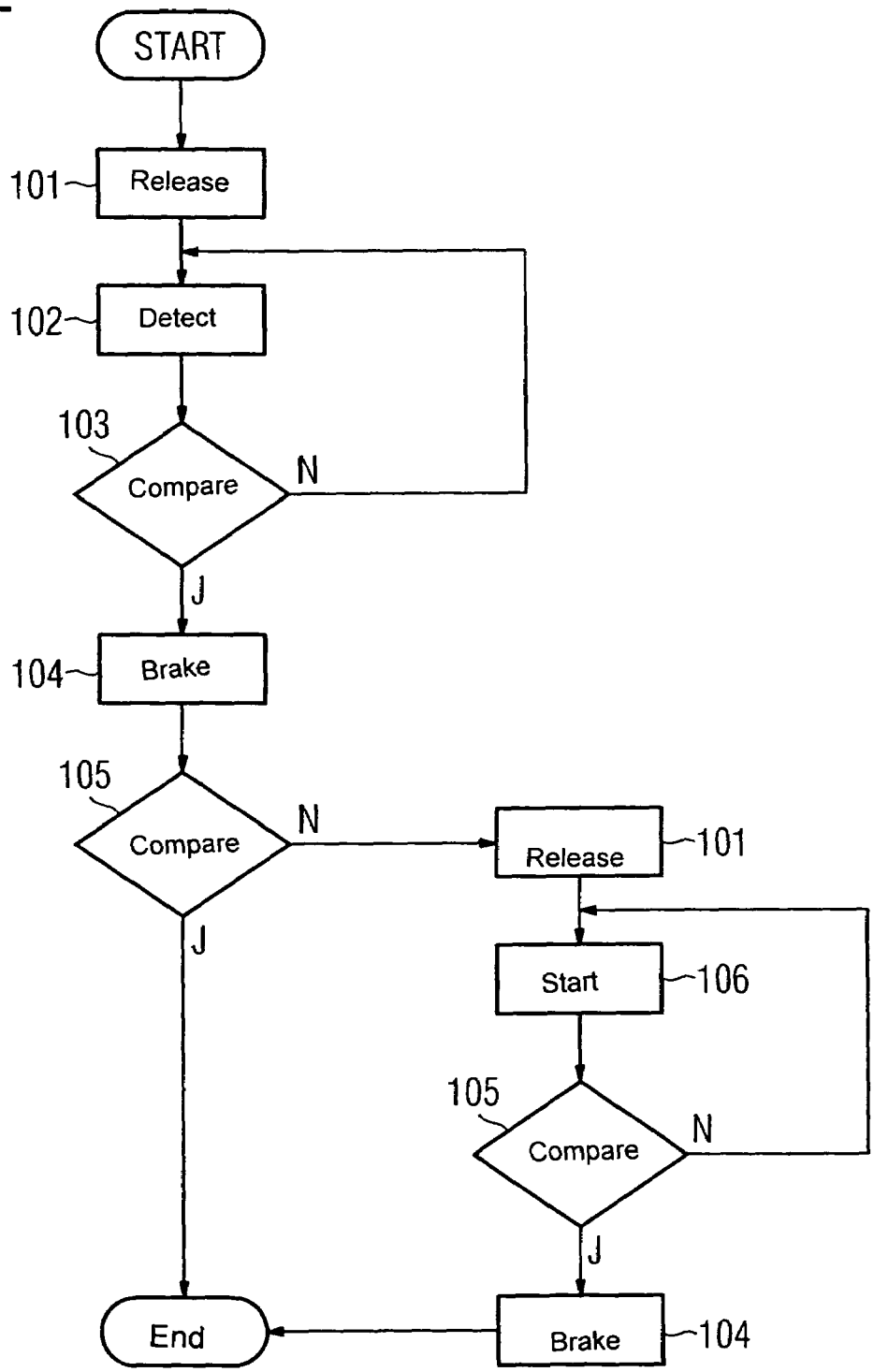
FIG. 2 is a schematic flow chart that illustrates a method for X-ray examination.

The method steps of FIG. 2 will be described hereinafter in conjunction with the system shown in FIG. 1, and reference numerals of system components refer to FIG. 1.

In one embodiment, a method for performing an X-ray diagnosis of an examination object includes activating an existing braking device 70 in order to fix the X-ray detector 31 in its position. If the user wants to displace and/or rotate the X-ray detector 31, then the method is started with the release of the brake 101. Releasing the brake can be done for instance by actuating a control key 50, for example, mechanically or by use of a touch screen. The control key 50 is disposed here on the X-ray emitter 30. Alternatively, in one embodiment, the brake is released only for as long as the key 50 is depressed by the user. In this embodiment, the key 50 that releases the brake is mounted on the component to be moved.

By releasing the brake, the X-ray detector 31 is made freely movable and can be moved by the user in the direction of a stop position 80. The position of the X-ray detector 31 is detected 102. The position of the X-ray detector 31 can be ascertained, for example, continuously or at periodic time intervals. After each ascertainment of a position, a comparison is made 103. The comparison 103 determines whether the detected position of the X-ray detector 31 is located within the predeterminably set stop region 81. If the detected position of the X-ray detector 31 is outside the stop region 81, then the X-ray detector 31 can be moved onward as before. Conversely, if the detected position of the X-ray detector 31 is located inside the predeterminably set stop region 81, then the X-ray detector 31 is braked and fixed 104. The braking and fixing are effected here by the braking device 70, which is embodied as a permanent-magnet brake. During the braking of the X-ray detector 31 to a standstill of the X-ray detector 31, the position of the X-ray detector 31 continues to be detected 102. After the moving X-ray detector 31 has been braked, the X-ray detector 31 is compared 105 with the predetermined stop position 80. If the position of the braked X-ray detector 31 matches the predetermined stop position 80, then the method for the X-ray detector 31 is terminated.

If a significant deviation of the position of the braked X-ray detector 31 from the preset stop position 80 exists and is detected by a control unit 60, then the fixation of the X-ray detector 31 is released again 101 by the control unit 60. A drive mechanism 90 embodied as an electric motor is started by the control unit 60 and sets the X-ray detector 31 in motion 106 in the direction of the predetermined stop position 80. The position of the X-ray detector 31 continues to be detected 102 and is compared 105 with the predetermined stop position 80. As long as the position of the X-ray detector 31 does not match the predetermined stop position 80, the X-ray detector 31 continues to be moved by the electric motor 90 in the direction of the stop position 80. As soon as the position of the X-ray detector 31 does match the predetermined stop position 80, the drive mechanism 90 is switched off and the braking device 70 is activated and the X-ray detector 31 is braked 104.

In one embodiment, the force from the brake that stops the component is selected to be great enough that upon activation of the brake, a virtually immediate standstill of the X-ray detector 31 is possible. With the tightening of the brake for X-ray detector 31 in the stop position 80, the method is terminated. The method can be repeated for a further component, such as the X-ray emitter 30, until all the components required for the X-ray diagnosis have been positioned in their intended stop positions. The X-ray examination can then be started.

In an alternate embodiment, constant detection of the position of moving components 30 and 31 is not necessary. In this exemplary embodiment, if the user wants to change the stop position of the X-ray emitter 30 from the vertical to the horizontal stop position, the brake for the X-ray emitter 30 is released, in method step 101. This is done here by pressing on a key that releases the brake, for example, the control key 50 for the X-ray emitter 30, by the user. For example, as long as the control key 50 is depressed, the brake of the X-ray emitter 30 is released. The user moves the X-ray emitter 30 in the direction of a predetermined horizontal stop position, not shown in FIG. 1. The user is given an output on the display 51 saying that the X-ray emitter 30 is now located in the stop region when the X-ray emitter 30 arrives in the stop region, not shown, around the horizontal stop position. The user thereupon lets go of the key 50 that releases the brake, and the X-ray emitter 30 is braked. The position detection can be activated either after the X-ray emitter 30 has been brought to a standstill, or already with the entry of the X-ray emitter 30 into the stop region. The current position of the X-ray emitter 30 is compared with the predetermined stop position, for example, in the control unit 60. The control unit 60 activates an electric motor 90, releases the brake of the X-ray emitter 30, and moves the X-ray emitter 30, using the electric motor 90 and continuous position detection, into the intended stop position. In this embodiment, the data processing effort and expense are reduced, since position data of the components 30 and 31 are ascertained only when these components are already positioned close to the respective predetermined stop position.

Various embodiments described herein can be used alone or in combination with one another. The forgoing detailed description has described only a few of the many possible implementations of the present invention. For this reason, this detailed description is intended by way of illustration, and not by way of limitation. It is only the following claims, including all equivalents that are intended to define the scope of this invention.

The invention claimed is:

1. A system for X-ray diagnosis of an examination object, the system comprising:
   a component that is manually movable relative to a support for the examination object, and
   at least one predeterminable stop position for the component,
   a position ascertaining device operative to ascertain a position of the component,
   a braking device operative to brake the manually movable component,
   a control unit connected to the position-ascertaining device and to the braking device, and
   a driving device that is operative to drive the component,
   wherein the braking device is operable to brake the manually movable component as a function of the position of the component relative to the stop position at a braked position,
   wherein the control unit is operable to determine a difference between the braked position and the stop position, and
   wherein the driving device is operable to move the component from the braked position to the stop position as a function of the difference between the braked position and the stop position.

2. The system for X-ray diagnosis of an examination object according to claim 1, wherein the component includes an X-ray emitter, X-ray detector, or both.

3. The system as defined by claim 2, wherein a driving device that is operative to drive the component is operatively connected to the control unit in such a way that the component is movable to the stop position.

4. The system as defined by claim 1, wherein a drive device that is operative to drive the component is operatively connected to the control unit in such a way that the component is movable to the stop position.

5. The system as defined by claim 4, wherein a coupling device is disposed between the drive mechanism and the movable component.

6. The system as defined by claim 4, wherein the drive device comprises an electric motor, or the braking device comprises a permanent-magnet brake.

7. The system as defined by claim 1, wherein a coupling device is disposed between the drive device and the movable component.

8. The system as defined by claim 7, wherein the X-ray emitter is rotationally movably supported, and a first and second stop positions are set such that an X-radiation from the X-ray emitter is projected in the vertical and horizontal directions.

9. The system as defined by claim 8, wherein the drive device comprises an electric motor, and the braking device comprises a permanent-magnet brake.

10. The system as defined by claim 7, wherein the drive device comprises an electric motor, or the braking device comprises a permanent-magnet brake.

11. The system as defined by claim 1, wherein a user interface is coupled to the control unit.

12. A method for performing an X-ray diagnosis of an examination object, the method comprising:
    moving a component, in the direction of a set stop position, the component being moved manually;
    detecting a position of the component;
    braking the manually moving component as soon as the position of the component reaches a predetermined stop region around the stop position with a braking device;
    determining a deviation between the braked position to the stop position with a control unit; and
    moving the component to the stop position as a function of the deviation with a drive device.

13. The method for performing an X-ray diagnosis of an examination object according to claim 12, wherein the component includes an X-ray emitter, an X-ray detector, or both.

14. The method for performing an X-ray diagnosis of an examination object according to claim 12, comprising sensing a speed of the component.

15. The method for performing an X-ray diagnosis of an examination object according to claim 12, wherein braking comprises braking with a braking device in response to a controller.

16. The method for performing an X-ray diagnosis of an examination object according to claim 12, wherein the manually moving component is operable to be combined with a motorized movement.

17. A system for X-ray diagnosis of an examination object, the system comprising:
    a component that is manually movable relative to a support for the examination object, and at least one predeterminable stop position for the component, a position ascertaining device operative to ascertain a position of the component, a braking device operative to brake the manually movable component, a control unit connected to the position-ascertaining device and to the braking device, and a drive device operatively connected to the control unit, the drive device being operative to drive the component to the at least one predeterminable stop position, wherein the braking device is activatable as a function of the position of the component relative to the stop position.

18. The system as defined by claim 17, wherein the drive device drives the component to the at least one predeterminable stop position after a manual movement of the component.

* * * * *